United States Patent
Tsuchiya et al.

(10) Patent No.: US 6,221,590 B1
(45) Date of Patent: Apr. 24, 2001

(54) METHOD FOR THE QUANTITATIVE DETERMINATION OF TELOMERASE ACTIVITY

(75) Inventors: Masayuki Tsuchiya; Ericka Savoysky; Ken-Ichi Akamatsu, all of Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 09/117,570
(22) PCT Filed: Jan. 31, 1997
(86) PCT No.: PCT/JP97/00245
§ 371 Date: Jul. 31, 1998
§ 102(e) Date: Jul. 31, 1998
(87) PCT Pub. No.: WO97/28281
PCT Pub. Date: Aug. 7, 1997

(30) Foreign Application Priority Data

Feb. 2, 1996 (JP) .................................... 8-017830

(51) Int. Cl.[7] .............................. C12Q 1/68; C12P 19/34; C07H 21/02
(52) U.S. Cl. .......................... 435/6; 435/91.1; 435/91.2; 435/174; 536/231; 536/24.3; 536/24.31; 536/24.33
(58) Field of Search .............................. 435/6, 91.1, 91.2, 435/174; 536/23.1, 24.3, 24.31, 24.33

(56) References Cited

U.S. PATENT DOCUMENTS

| | | | |
|---|---|---|---|
| 5,534,406 | * 7/1996 | Liang et al. | 435/5 |
| 5,645,986 | * 7/1997 | West et al. | 435/6 |
| 5,837,453 | * 11/1998 | Harley et al. | 435/6 |
| 5,856,096 | * 1/1999 | Windle et al. | 435/6 |

OTHER PUBLICATIONS

Savoysky et al, "Detection of telomerase activity by combination of TRAP method and scintillation proximity assay (SPA)", Nucleic Acids Research 24(6):1175–1176, Mar. 1996.*
Amersham catalog, pp. 252–257, 1995.*
Serres et al, "Development of a novel scintillation proximity competitive hybridization assay for the determination of phosphorothioate antisense oligonucleotide plasma concentrations in toxicokinetic study", Anal. Biochem. 233:228–233, Jan. 1996.*
Bosworth et al, "Scintillation proximity assay", Nature 341:167–168, Sep. 1989.*
Morin, G.B., The Human Telomere Terminal Transferase Enzyme is a Ribonucleoprotein That Synthesizes TTAGGG Repeats, Cell, vol. 59, pp. 521–529 (Nov. 1989).
E. Savoysky, et al., Detection of Telomerase Activity by Combination of TRAP Method and Scintillation Proximity Assay (SPA), Nucleic Acids Research, vol. 24, No. 6, pp. 1175–1176 (1996).
A. Schoenfeld, et al., Semiquantification of Polymerase Chain Reaction Product Using a Bead Scintillation Proximity Assay and Comparison with the Southern Blot Method, Analytical Biochemistry, vol. 228, pp. 164–167 (1995).
N. W. Kim, et al., Specific Association of Human Telomerase Activity with Immortal Cells and Cancer, Science, vol. 266, pp. 2011–2015 (1994).
B.K. Rawal, et al., Quantification of Cytomegalovirus DNA in Blood Specimens from Bone Marrow Transplant Recipients by the Polymerase Chain Reaction, Journal of Virological Methods vol. 47, pp. 189–202 (1994).
D.S. Hughes, et al., Quantification of Latent Mamestra Brassicae Nuclear Polyhedrosis Virus in M. Brassicae Insects Using a PCR–Scintillation Proximity Assay, Journal of Virological Methods, vol. 50, pp. 21–28 (1994).

* cited by examiner

Primary Examiner—Jeffrey Fredman
(74) Attorney, Agent, or Firm—Davidson, Davidson & Kappel, LLC

(57) ABSTRACT

A method for the quantitative determination of telomerase activity comprising: amplifying an oligonucleotide sequence synthesized by a DNA synthesis reaction with a telomerase, using a primer modified with either of two materials capable of mutually binding to each other, in the presence of a radioisotope element; allowing the resulting reaction product to bind to a fine particle previously coated with the other of said two materials capable of mutually binding to each other; and measuring scintillation generated from the fine particle due to said binding to quantitatively determine the telomerase activity.

15 Claims, 5 Drawing Sheets

METHOD FOR THE QUANTITATIVE DETERMINATION OF TELOMERASE ACTIVITY

TECHNICAL FIELD

The present invention relates to a method for the quantitative determination of telomerase activity.

BACKGROUND ART

Telomerase is known to be an enzyme which catalyzes the extension of the telomere terminal end (terminal portion of a linear chromosome) and many studies thereon have been conducted: Greider C. W. and Blackburn E. H., (1987) Cell, 51, 887–898; Morin G. B. (1989) Cell, 59, 521–529.

The activity of telomerase is not detected in normal cells except in certain cells such as hemopoietic stem cells, while strong telomerase activity can be detected in most cancer cells. Telomerase is considered to be associated with the maintenance of infinite proliferation of cancer cells. Thus, the detection and quantitative determination of the telomerase activity is important in the diagnosis of cancer. Further, an inhibitor therefor may be expected to be an anti-cancer agent with little side-effect on normal cells: Counter C. M. et al., (1989) EMBO J., 11, 1921–1929; Counter C. M. et al., (1994) Proc. Natl. Acad. Sci. USA, 91, 2900–2904; Chadeneau C. et al., (1995) Cancer Res., 55, 2533–2536;

Hiyama E. et al., (1995) Nature Med., 1, 249–255, Shay J. W. et al., (1995) Mol. Cell. Biol., 15, 425–432.

Recently, the detection of telomerase has been studied by using a ciliate Tetrahymena (Greider and Blackburn, 1985; 1987; 1989). In these studies, telomerase was detected in a single primer extension assay system. Substrates required for such an assay are the single-stranded telomere oligonucleotide sequence $(TTGGGG)_3$, dGTP, dTTP and dGTP labelled with $^{32}P$. The repeat of TTGGGG which is the telomere sequence of Tetrahymena is added to the 3' end of the oligonucleotide primer during short incubation at room temperature. Then, the reaction product is detected by electrophoresis and autoradiography. This assay has enabled the study on the kinetics and primer specificity of telomerase derived from Tetrahymena and other ciliates, and the cloning of telomerase RNA (Romero and Blackburn, 1991; Lee and Blackburn, 1993, Collins and Greider, 1993; Autexier and Greider, 1994).

On the other hand, the number of human telomeres is as small as 92 and it has been considered that it is impossible to detect the telomerase activity. However, the telomerase activity was found in the telomerase assay using extracts of Hela cell line derived from human cervical cancer and it was elucidated that the enzyme adds a number of TTAGGG repeat sequences to the 3' end of telomere (Morin, 1989). It has been suggested that telomerase is an enzyme conserved in all eucaryotic cells and is markedly activated in human tumor cells (Counter et al., 1992; 1994).

In the conventional assay systems, however, there are problems in the sensitivity, time period required for detection, quantitativeness and dealing of a large amount of sample (Counter et al., 1994).

Recently, the sensitivity and detection time have been improved by the means based on the polymerase chain reaction called as TRAP (telomeric repeat amplification protocol): Kim N. W. et al., (1994) Science, 206, 2011–2015; Piatyszek M. A. et al., (1995) Meth. Cell Sci., 17, 1–15.

This technique involves the telomerase reaction and polymerase chain reaction followed by the detection of reaction products by polyacrylamide gel electrophoresis and autoradiography. The quantitative determination of telomerase activity is performed by measuring the intensities of appearing bands with a densitometer or other means and comparing them with known amounts of, e.g., Hela cell extracts, used as a control.

This method has improved the sensitivity, enabling the detection of telomerase activity even in a small number of cells, such as 100 cells. That is to say, the sensitivity of detection of telomerase activity can be increased $10^4$ times as compared with conventional assay methods; the sensitivity has been greatly improved as compared with the conventional techniques.

Even in this TRAP method, however, analysis of $^{32}P$- or fluorescence-labelled reaction products by polyacrylamide gel electrophoresis, HPLC or other means is still required, so that the number of samples to be measured is limited. Further, in the case of $^{32}P$, its handling has problems such as treatment or disposal of gel or a large amount of waste liquid. In addition, it will take a long time to conduct a series of operations such as preparation of the gel, electrophoretic separation (analysis) and exposure or detection (usually 2 to 48 hours). Subsequently, the intensities of the detected bands must be measured by a densitometer or other means. Thus, there has been a problem of delay in obtaining the results.

These problems are very inconvenient, in particular in the diagnosis of progression and prognosis of cancer which requires real time analysis, and are also inconvenient in the analysis of a large amount of samples.

DISCLOSURE OF INVENTION

It is an object of the present invention to provide a method enabling rapid detection and quantitative determination of telomerase activity with a high sensitivity.

The present inventors have eagerly studied the above problems and, as a result, found that telomerase activity can be rapidly detected and quantitatively determined with a high sensitivity by constructing a system comprising the DNA synthetic reaction with teromerase in combination with the scintillation proximity assay technology (SPA) developed by Amersham (Bothworth N. and Towers P. (1989) Nature, 341, 167–168), leading to the completion of the present invention.

That is to say, the present invention is a method for the quantitative determination of telomerase activity comprising: amplifying an oligonucleotide sequence which has been synthesized by a DNA synthesis reaction with a telomerase, using a primer modified with either of two materials capable of mutually binding to each other, in the presence of a radioisotope element; making the resulting sequence to bind to a fine particle which has been previously coated with the other of said two materials capable of mutually binding to each other; and measuring scintillation generated from the fine particle due to said binding to quantitatively determine the telomerase activity.

Further, the present invention is a method for the quantitative determination of telomerase activity comprising: carrying out a DNA synthesis reaction with a telomerase, using a primer modified with either of two materials capable of mutually binding to each other, in the presence of a radioisotope element; making the resulting reaction product to bind to a fine particle which has been previously coated with the other of said two materials capable of mutually binding to each other; and measuring scintillation generated from the fine particle due to said binding to quantitatively determine the telomerase activity.

The two materials capable of mutually binding to each other as used herein include biotin and avidin.

Hereinafter the present invention will be described in detail.

The present invention is a method for detecting and quantitatively determining telomerase activity in cell extracts. The present invention involves a method for amplifying an oligonucleotide sequence (telomere repeat sequence) synthesized by a DNA synthesis reaction with a telomerase, using a primer modified with either one of two materials capable of mutually binding to each other, in the presence of a radioisotope. However, a method for reacting without amplification of the telomere repeat sequence is also included in the present invention. Then, the resulting reaction product is allowed to bind to a fine particle which has been previously coated with the other of said two materials capable of mutually binding to each other and scintillation generated from the fine particle due to said binding is measured to quantitatively determine the telomerase activity.

(1) Amplification of Telomere Repeat Sequence by Cell Extracts

The telomere repeat sequence may be amplified by, for example, the polymerase chain reaction method. The polymerase chain reaction provides detection results with a high sensitivity.

The polymerase chain reaction is effected using an oligonucleotide primer modified at 5' end thereof with one of the two materials capable of mutually binding to each other, in the presence of a radioisotope, for example, $^3$H or $^{125}$I.

The "two materials capable of mutually binding to each other" may include, for example, an enzyme and a substrate, biotin and avidin, an antigen and an antibody, a lectin and its receptor, a hormone and its receptor, a neurotransmitter and its receptor, and the like.

The primer may be designed depending upon the telomere sequence to be amplified. For example, the primer as shown in SEQ ID NO. 1 (TS primer) and the primer as shown in SEQ ID NO. 2 (CX primer) are included. A ligand such as biotin may be linked to the 5' end of the primer by any known method. This technique may be performed in a usual assay buffer.

In the DNA synthesis reaction with a telomerase, the use of a primer labelled with, e.g., biotin, enables direct detection of a freshly synthesized oligonucleotide sequence by SPA technique.

(2) Preparation of Fine Particles

The fine particles which may be used herein include, for example, SPA beads attached to the reverse transcriptase activity detection kit supplied by Amersham (Product Number NK9020).

(3) Binding Reaction of Extended Oligonucleotide Sequence and Fine Particles, and Detection Then, the extended oligonucleotide sequence amplified by the polymerase chain reaction is linked to fine particles which have been previously coated with the other of the above described two materials capable of mutually binding to each other. When the primer is biotinated, the fine particles used may be coated with streptavidin which is the other material of said two materials capable of mutually binding to each other. As a result of binding of the amplified oligonucleotide to the fine particles, the fine particles are stimulated by low eneregy β rays emitted from $^3$H or $^{125}$I, resulting in the emission of light from the fine particles (scintillation), since the amplified oligonucleotide is labelled with a radioisotope such as $^3$H or $^{125}$I. The scintillation as a signal can be measured to detect the presence of an oligonucleotide of concern.

The intensity of the signal detected is proportional to the amount of the reaction products bound to the fine particles, i.e., the activity of the telomerase. Accordingly, a higher signal means a higher activity of the telomerase.

The telomerase activity is quantitatively determined by measuring the fluorescence intensity according to the above using a standard sample as a control.

(4) According to the method of the present invention, telomerase activity may also be detected without using the said amplification method. For example, the oligonucleotide sequence synthesized by a DNA synthesis reaction with a telomerase is reacted using a primer modified with either one of two materials capable of mutually binding to each other in the presence of a radioisotope. Then, the resulting reaction product is linked to fine particles which have been previously coated with the other of said two materials capable of mutually binding to each other and scintillation generated from the fine particles due to said linkage is measured to quantitatively determine the telomerase activity.

The meaning of the "two materials capable of mutually binding to each other", the preparation of fine particles, and the linking reaction of extended oligonucleotide sequence and fine particles as well as the detection are the same as above described.

According to the present invention, a significantly higher sensitivity is achieved as compared with conventional detection methods. Further, low energy β-emission is only required, so that no special equipment for disposal is required and it is also not necessary to separate the reaction products from radioisotopes which have not been incorporated thereinto. Consequently, there is provided one of major improvements that detection can be rapidly performed. Thus, results may be obtained within one hour in the method of the present invention, so that all processes for measurement can be completed in one day.

As stated above, according to the present invention, the telomerase activity may be easily determined quantitatively with good reproducibility and a large amount of samples can be handled with ease.

For example, quantitative determination of telomerase activity in tissues obtained clinically is very useful to diagnose cancers and to monitor the progression of the cancer and the prognosis of treatment (Hiyama et al., 1995).

BEST MODE FOR CARRYING OUT THE INVENTION

Figure 1:
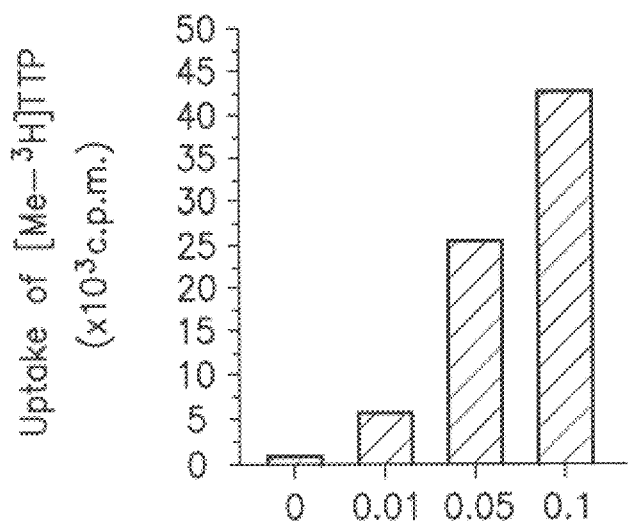
FIG. 1 shows the detection results according to the present invention in relation to the primer concentration.
Figure 1:
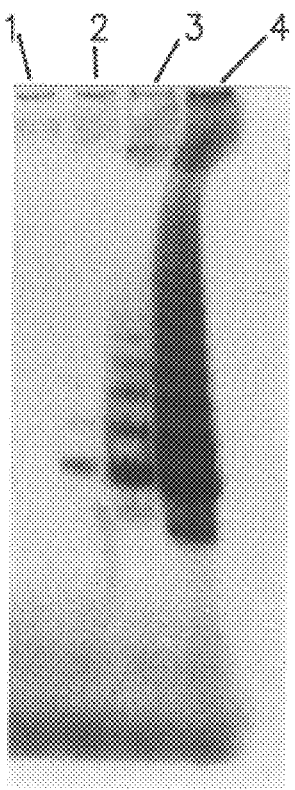

Hereinafter, the present invention will be illustrated by way of examples. However, the present invention is not limited to these examples.

EXAMPLE 1

I. Materials and Method (1) Preparation of Cell Extract

Cell extracts were prepared by a known method (Kim N. W. et al., (1994) Science, 206, 2011–2015) with several modifications. Human erythroleukemia cell line HEL was cultivated and cells in the logarithmic growth phase were centrifuged at 2000 rpm for 5 minutes to collect the cells. The cells were washed twice with ice-cooled PBS and once with ice-cooled, RNase-free washing buffer (10 mM Hepes pH 7.5, 1 mM $MgCl_2$, 10 mM KCl, 1 mM DTT). The cell pellet was re-suspended at $5\times10^5$ cells/µl in RNase-free lytic buffer (10 mM Tris-HCl pH 7.5, 1 mM $MgCl_2$, 1 mM EGTA, 0.1 mM PMSF, 5 mM β-mercaptoethanol, 0.5% CHAPS (Cholamidopropyl-dimethyl-ammonio-1- propanesulfonate) and 10% glycerol). The suspension was lightly stirred, incubated on ice for 30 minutes, and centrifuged at 15,000 rpm for 30 minutes to remove impurities in the lysate. The supernatant was divided into small portions and stored at −80° C.

(2) Synthesis of primers

TS primer (SEQ ID NO. 1) and CX primer (SEQ ID NO. 2) were synthesized using a DNA synthesizer of ABI. The biotinated CX and TS primers were synthesized by coupling biotin LC biotin-ON™ phosphoramidite (Clontech) to the 5' end of the oligonucleotides. The primers were purified using ABI OPC column according to the manufacturer's instructions, lyophilized and re-suspended in water treated with DEPC (diethylpyrocarbonate).

(3) Quantitative Detection of Telomerase Activity by TRAP/SPA

The TRAP/SPA assay according to the present invention was carried out in a known method (Kim N. W. et al., (1994) Science, 206, 2011–2015; Piatyszek M. A. et al., (1995) Meth. Cell Sci., 17, 1–15) with several modifications as follows.

A predetermined amount (0, 0.01, 0.05, 0.1 µg/assay) of biotinated CX primer (Biot-CX) was trapped under a wax layer of Hot-Start tube (GIBCO-BRL).

Then, in the DNA synthesis reaction with the telomerase, 2 µl of the cell extract ($10^4$ cells) was incubated on a wax barrier in 50 µl of a final reaction mixture containing 20 mM Tris-HCl pH 8.3, 1.5 mM $MgCl_2$, 63 mM KCl, 0.005% Tween 20, 1 mM EGTA, 50 µM dATP and dCTP each, 2 µM dTTP, 50 µM dGTP, 2 µCi [Me-$^3$H] TTP (Amersham, 114 Ci/mmol), 0.1 µg/pl BSA, 2 U Taq polymerase and 0.1 µg or a predetermined amount of TS primer, at room temperature for 30 minutes.

Then, to amplify the synthesized telomere oligonucleotide, the mixture was heated at 90° C. for 90 seconds and 31 cycles of polymerase chain reaction were carried out with each cycle comprising at 94° C. for 30 seconds, at 50° C. for 30 seconds and at 72° C. for 45 seconds.

In case of a large amount of samples, particularly in the case using 96 well microtiter plate, the assay was carried out without wax barrier, Biot-CX was added immediately before the polymerase chain reaction, and the mixture was covered with mineral oil.

The reaction product (40 µl) was transferred to 96 well plate (Wallac), and 50 µl of fine particles Fluoromicrosphere coated with streptavidin (1:4 solution in 0.56 MEDTA) was added and incubated at 37° C. for 10 minutes to link the biotinylated, $^3$H- labelled reaction product to the streptavidin beads.

The plate was counted on MicroBeta scintillation counter (Wallac).

For comparison, conventional TRAP (TRAP in combination with polyacrylamide gel electrophoresis, TRAP-PAGE) was effected as follows.

The above procedures were followed except that the biotinated primer was replaced with a non-biotinated CX primer, the dGTP concentration was changed to 20 µM, dTTP was increased to 50 µM, and 2 µCi [Me-$^{32}$H] TTP (Amersham, 114 Ci/mmol) was replaced with [β-$^{32}$P] dGTP (Amersham, 800 Ci/mmol).

After the polymerase chain reaction, the reaction product was subjected to 10% polyacrylamide gel electrophoresis (SDS-PAGE) in 0.3×TBE and exposed to Phosphorimager (Fuji Imaging Plate) to analyze the reaction product (40 µl).

(4) DNA Synthesis Reaction with Telomerase/Quantitative Detection of Telomerase Activity by SPA First, as a telomere extension reaction, 50 µl of a reaction liquid containing HEL cell CHAPS extracts (corresponding to $10^4$ and $10^5$ cells), 20 mM Tris-HCl, 1.5 mM $MgCl_2$, 63 mM KCl, 0.005% Tween 20, 1 mM EDTA, 50 µM DATP and dGTP each, 1 µM dTTP, 2 µCi [Me-$^3$H] TTP (Amersham, 114 Ci/mmol), 0.1 µg BSA, and 0.1 µg of biotinated primer $(TTAGGG)_4$ was incubated at room temperature for 30 minutes.

Then, the reaction product (40 µl) was transferred to 96 well plate, mixed with 50 µ of fine particles Fluoromicrosphere coated with streptavidin (1:4 solution in 0.56 M EDTA), and incubated at 37° C. for 10 minutes to link the biotinated, $^3$H-labelled reaction product to the streptavidin beads.

This was counted on MicroBeta scintillation counter (Wallac).

For comparison, detection was conducted by conventional polyacrylamide gel electrophoresis followed by autoradiography.

In the above mentioned telomerase reaction mixture, the dGTP concentration was changed to 5 µM, 2 µCi of (β32P) dGTP (Amersham, 800 Ci/mmol) was added, and the dTTP concentration was increased to 50 µM.

The reaction product (40 µl) was electrophoresed on 8% polyacrylamide gel containing 7 M urea and exposed to an imaging plate for 4 days.

II. Results (1) Effect of Primer Concentration

The effects of primer concentrations were the same in both the method of the present invention and the conventional method (FIG. 1, upper and lower panels). In the electrophoresis shown in FIG. 1, lower panel, lanes 1 to 4 are primer concentrations 0, 0.01, 0.05 and 0.1 µg/assay, respectively, which correspond to the primer concentrations in FIG. 1, upper panel.

Thus, it is shown that according to the method of the present invention, telomerase activities can be detected and quantitatively determined without carrying out autoradiography after electrophoresis.

(2) Sensitivity of the Method According to the Present Invention

Figure 2:
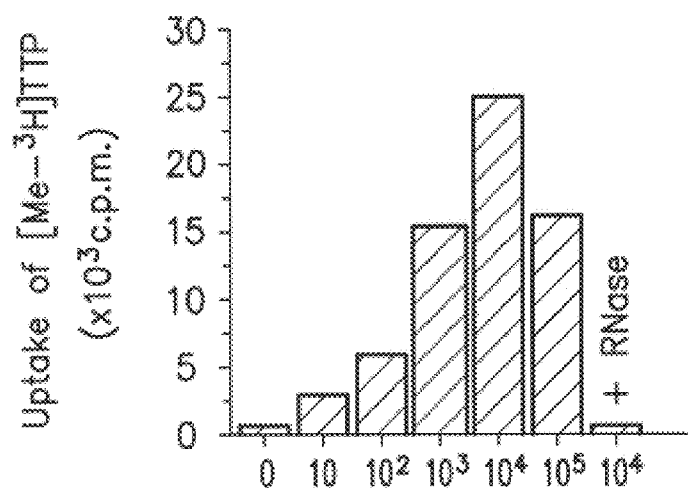
FIG. 2 shows the detection results according to the present invention in relation to the number of cells.
Figure 2:
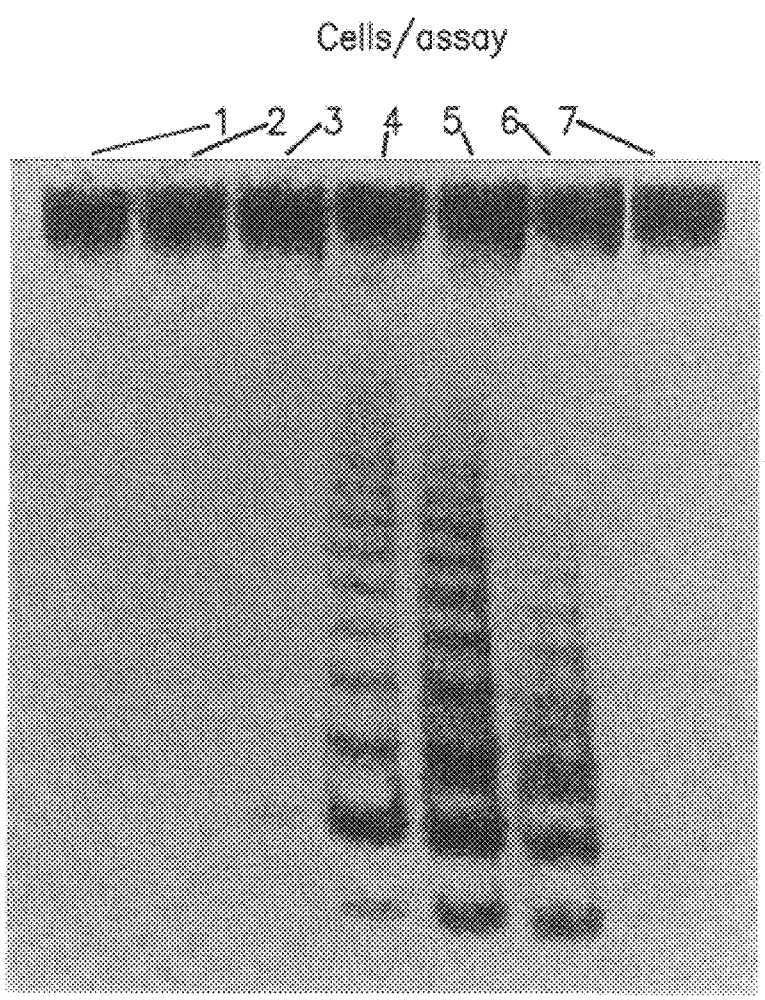

The sensitivity of the SPA detection according to the present invention was determined by comparing with conventional TRAP assay (TRAP-PAGE) where HEL CHAPS extracts (CHAPS extracts of HEL cells) were stepwise diluted. The detection limit is about 100 cells per assay (FIG. 2, lower panel) in the conventional TRAP-PAGE assay, whereas in the TRAP-SPA assay of the present invention, the telomerase activity can be clearly detected even in only 10 cells (FIG. 2, upper panel). Lanes 1 to 7 in FIG. 2, lower panel correspond to 0, 10, $10^2$, $10^3$, $10^4$ and $10^5$ cells/assay and a mixture of $10^4$ and RNase, respectively, in FIG. 2, upper panel.

Figure 3:
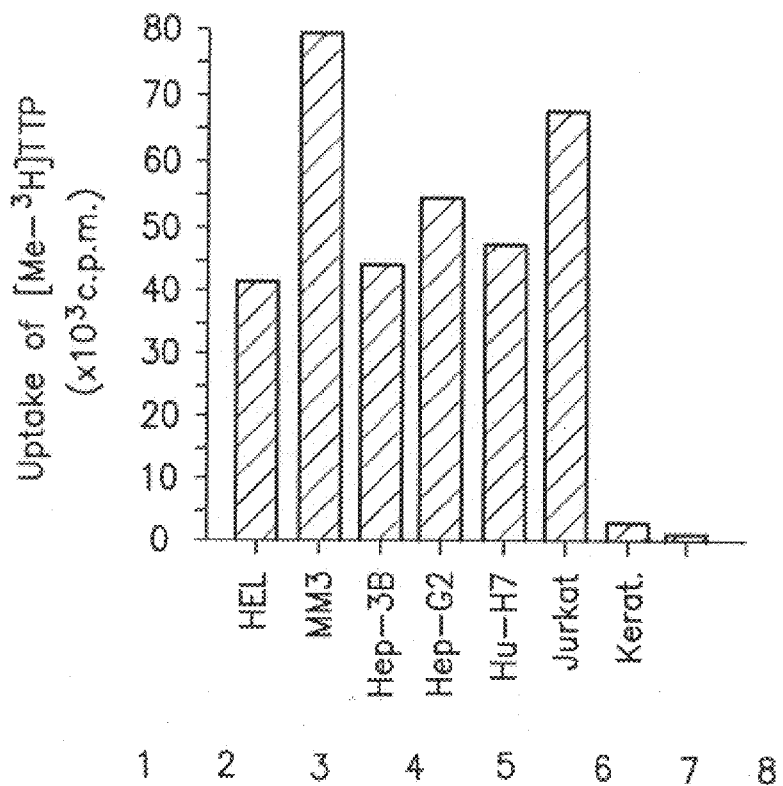
FIG. 3 shows the detection results according to the present invention in relation to various cells.
Figure 3:
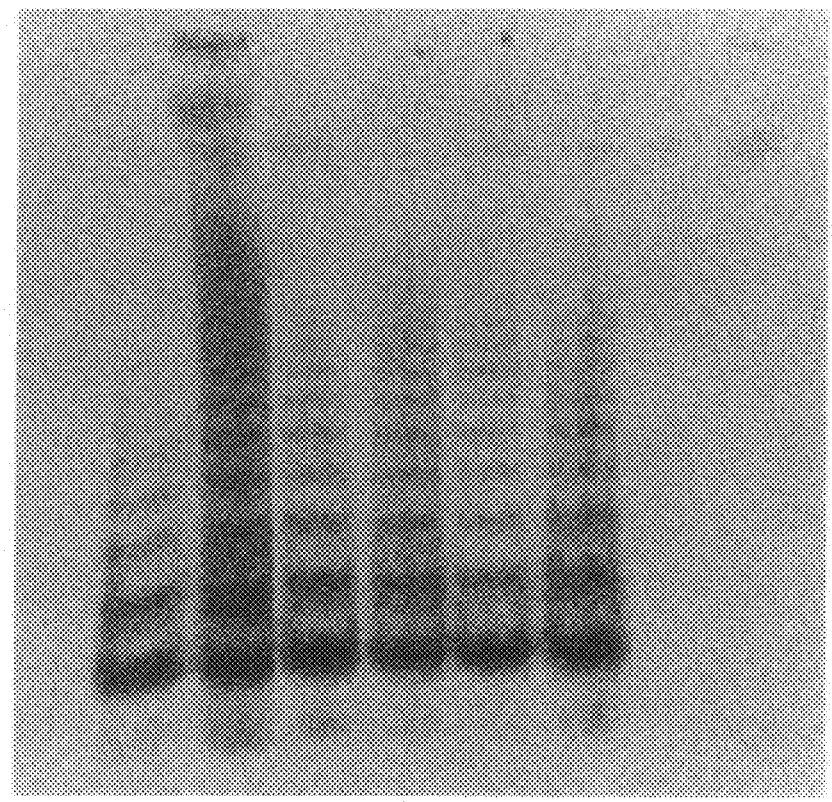

Further, similar results were obtained even in multiple myeloma (MM3), liver cancer (Hep-3B, Hep-G2, Hu-H7), and other cell lines, such as Jurkat cells, preliminarily screened by TRAP-PAGE and observed uptakes were substantially in complete accordance with the respective intensities of the band pattern in polyacrylamide gel (FIG. 3). The strongest signal was obtained from multiple myeloma in both the method of the present invention and the conventional method, while no activity was detected in keratinocytes, normal cells, used as a control. Lanes 1 to 8 in FIG. 3, lower panel correspond to each cells HEL, MM3, Hep-3B, Hep-G2, Hu-H7, Jurkat and Kerat. and cell-free control.

Accordingly, the telomerase activity can be detected quantitatively with a high sensitivity according to the method of the present invention.

Figure 4:
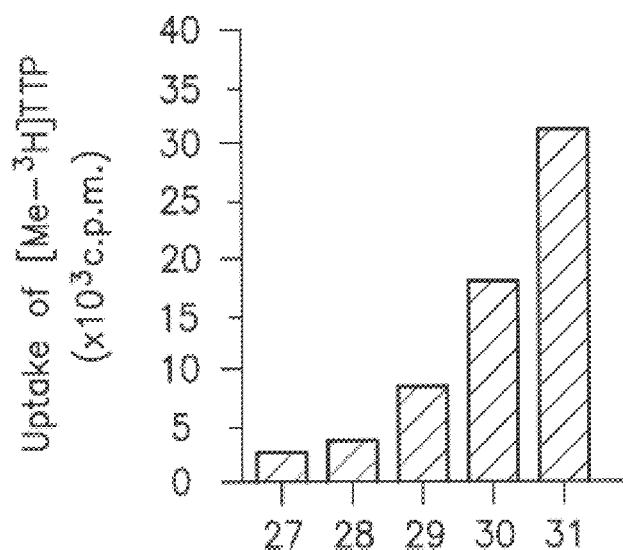
FIG. 4 shows the detection results according to the present invention in relation to the number of cycles in the polymerase chain reaction.
Figure 4:
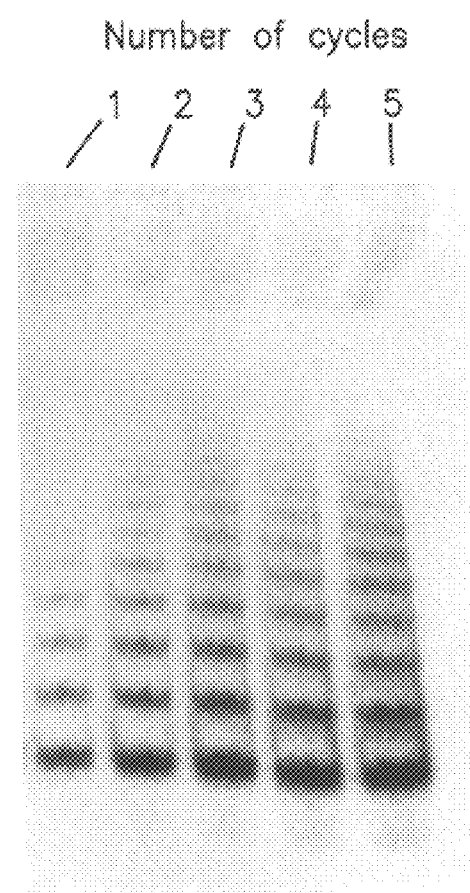

The effect of the number of cycles in the polymerase chain reaction on the accumulation of telomerase products was also compared between the method of the present invention and the conventional method. Significant uptake of $^3$H was observed in the band pattern of the gel electrophoresis or SPA after at least 27 cycles of amplification (FIG. 4). The intensity of detected signals increased with the number of cycles in both cases; thus, a very good relationship between the two methods was obtained. In FIG. 4, lower panel, lanes 1 to 5 correspond to the number of cycles in upper panel, 27, 28, 29, 30 and 31, respectively.

Figure 5:
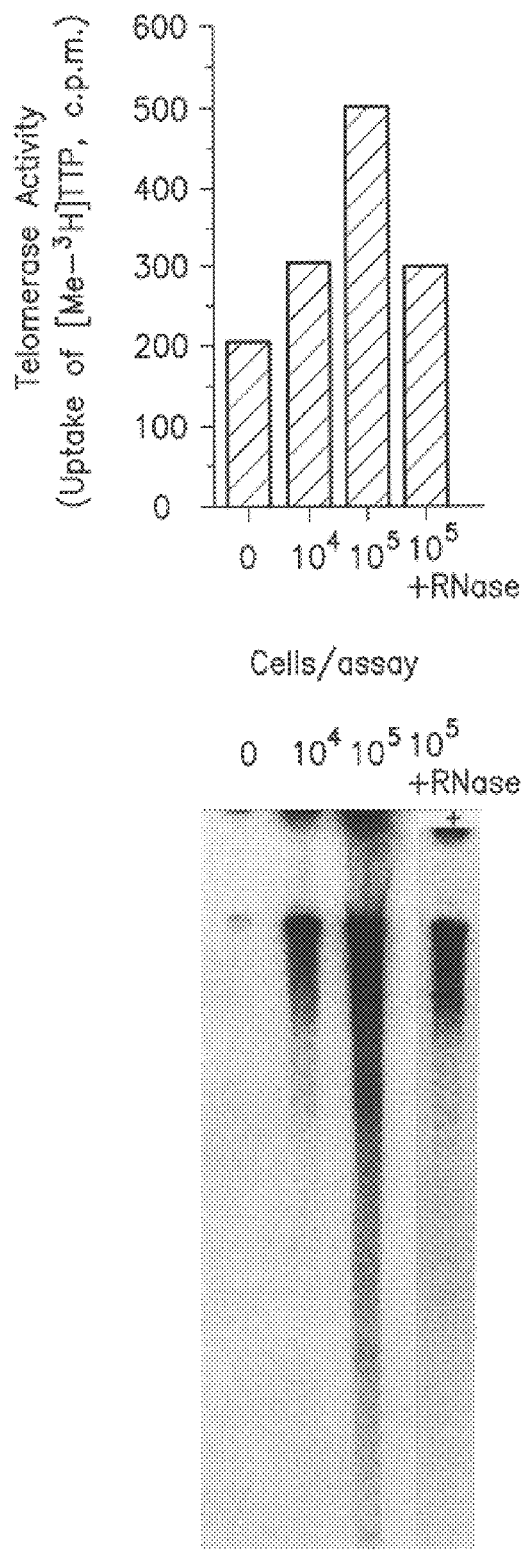
FIG. 5 shows the detection results according to the present invention in relation to the number of cells.

(3) DNA Synthetic Reaction by Telomerase—Quantitative Detection of Telomerase Activity Even when the telomere repeat sequence was not amplified, telomerase activity could be detected and quantitatively determined in a similar manner (FIG. 5). As shown in FIG. 5, the telomerase activity in relation to the number of cells was similar in both the method of the present invention (upper) and the conventional method (lower).

Industrial Applicability

According to the present invention, there is provided a method enabling the rapid and highly sensitive detection and quantitative determination of telomerase activity.

What is claimed is:

1. A method for the quantitative determination of telomerase activity comprising the steps of:
   a) performing a DNA synthesis reaction using a telomerase;
   b) amplifying the telomerase synthesis product by the Polymerase Chain Reaction using radiolabeled nucleotides and a primer which has been modified with either of two materials which bind to each other;
   c) allowing the resulting reaction product to bind to a fine particle comprising a scintillant that was previously coated with the other of said two materials which bind to each other; and
   d) measuring scintillation generated by the fine particle due to the bound radiolabeled oligonucleotide to quantitatively determine the telomerase activity.

2. A method for the quantitative determination of telomerase activity comprising the steps of:
   a) performing a DNA synthesis reaction using a telomerase and a telomerase primer which has been modified with either of two materials which bind to each other, wherein the synthesis reaction is in the presence of radiolabeled nucleotides;
   b) allowing the resulting reaction product to bind to a fine particle comprising a scintillant that was previously coated with the other of said two materials which bind to each other; and
   c) measuring scintillation generated by the fine particle due to the bound radiolabeled oligonucleotide to quantitatively determine the telomerase activity.

3. The method for the quantitative determination of telomerase activity of claim 1, wherein the two materials which bind to each other are biotin and avidin or streptavidin.

4. The method for the quantitative determination of telomerase activity of claim 2, wherein the two materials which bind to each other are biotin and avidin or streptavidin.

5. The method of claim 1, wherein the fine particle comprising scintillant consists of fluoromicrospheres.

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: TS primer

<400> SEQUENCE: 1
aatccgtcga gcagagtt                                                 18

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: CX primer

<400> SEQUENCE: 2
cccttaccct taccctaacc ctaa                                          24

6. The method of claim 1, wherein the fine particle comprising scintillant consists of Scintillation Proximity Assay beads.

7. The method for the quantitative determination of telomerase activity of claim 1, wherein the two materials which bind to each other are a lectin and its receptor.

8. Tie method for the quantitative determination of telomerase activity of claim 1, wherein the primer is selected from the group consisting of SEQ ID NO:1 and SEQ ID NO:2.

9. The method of claim 2, wherein the fine particle comprising scintillant consists of fluoromicrospheres.

10. The method of claim 2, wherein the fine particle comprising scintillant consists of Scintillation Proximity Assay beads.

11. The method for the quantitative determination of telomerase activity of claim 2, wherein the two materials which bind to each other are a lectin and its receptor.

12. The method for the quantitative determination of teromerase activity of claim 2, wherein the primer comprises the nucleotide sequence $(TTAGGG)_4$.

13. The method for the quantitative determination of telomerase activity of claim 1, wherein the primer is modified at the 5' position with biotin and the fine particle comprising a scintillant is coated with avidin or streptavidin.

14. The method for the quantitative determination of telomerase activity of claim 2, wherein the primer is modified with biotin and the fine particle comprising a scintillant is coated with avidin or streptavidin.

15. A method for the quantitative determination of telomerase activity comprising the steps of:

a) performing a DNA synthesis reaction using a telomerase and a primer which has been modified with either of two materials which bind to each other;

b) amplifying the telomerase synthesis product by the Polymerase Chain Reaction using radiolabeled nucleotides and a primer which has been modified with either of two materials which bind to each other;

c) allowing the resulting reaction product to bind to a fine particle comprising a scintillant that was previously coated with the other of said two materials which bind to each other; and d) measuring scintillation generated by the fine particle due to the bound radiolabeled oligonucleotide to quantitatively determine the telomerase activity.

* * * * *